US009535051B2

(12) United States Patent
Markee

(10) Patent No.: US 9,535,051 B2
(45) Date of Patent: Jan. 3, 2017

(54) METHOD AND APPARATUS FOR MEASURING AND RECORDING REAL TIME ENVIRONMENTAL CONDITIONS AT TARGET SHELL LOCATIONS DURING THE SHELL BUILDING PROCESS

(71) Applicant: Julie Markee, La Center, WA (US)

(72) Inventor: Julie Markee, La Center, WA (US)

( * ) Notice: Subject to any disclaimer, the term of this patent is extended or adjusted under 35 U.S.C. 154(b) by 111 days.

(21) Appl. No.: 14/046,888

(22) Filed: Oct. 4, 2013

(65) Prior Publication Data

US 2014/0096592 A1   Apr. 10, 2014

Related U.S. Application Data

(60) Provisional application No. 61/710,613, filed on Oct. 5, 2012.

(51) Int. Cl.
   *G01N 33/38*   (2006.01)
   *G01N 1/22*   (2006.01)

(52) U.S. Cl.
   CPC ........... *G01N 33/388* (2013.01); *G01N 1/2205* (2013.01)

(58) Field of Classification Search
   CPC ................ G01N 33/388; G01N 1/2205; G01N 2001/2229; G01N 2001/2232; G01N 2001/2261; G01N 2001/2285; G01N 2001/2288; G01N 7/14; G01N 33/206; G01K 1/08; G01K 1/01; G01K 1/12
   See application file for complete search history.

(56) References Cited

U.S. PATENT DOCUMENTS 4,317,995 A * 3/1982 Bradshaw .......... G01N 33/0014
                                                    250/286
5,044,770 A    9/1991 Haghkar
                    (Continued)

FOREIGN PATENT DOCUMENTS

| CA | WO 2010069030 A1 * | 6/2010 | ........... G01N 1/2205 |
| WO | WO03/043858 | 5/2003 | |
| WO | WO 2011070535 A1 * | 6/2011 | |

OTHER PUBLICATIONS

Zachary Charles Grasley, Internal Relative Humidity, Drying Stress Gradients, and Hygrothermal Dilation of Concrete, Portland Cement Association, 2001, Michigan Technological University, Urbana, Illinois.

(Continued)

*Primary Examiner* — Lisa Caputo
*Assistant Examiner* — Punam Roy
(74) *Attorney, Agent, or Firm* — Robert Ireland

(57) ABSTRACT

An investment casting shell substrate sensor method and apparatus comprising a hollow probe 10 having an aperture 30, the aperture 30 covered by a water proof breathable membrane (WPBM) 20 that is constructed and arranged to repel liquid from entering the aperture 30, while remaining permeable so as to allow vapor and air to pass through the aperture 30, thereby creating a liquid free internal void 50 within the hollow probe 10 that receives a sensor 40 for measuring the conditions (i.e. temperature and humidity) within the internal void 50, which are accurately indicative of the conditions at the shell substrate at the aperture 30 location. The disclosed sensor assembly provides target specific information at selected substrates within the shell real time, during the shell building process.

5 Claims, 5 Drawing Sheets

(56) References Cited

U.S. PATENT DOCUMENTS

| | | | |
|---|---|---|---|
| 6,000,845 | A | 12/1999 | Tymkewicz et al. |
| 8,441,269 | B2 | 5/2013 | Minh et al. |
| 2003/0179809 | A1* | 9/2003 | Nakagawa ............... G01K 1/08 374/158 |
| 2007/0266800 | A1* | 11/2007 | Risk ......................... G01N 1/22 73/863.23 |
| 2010/0011838 | A1* | 1/2010 | Yamada ............. G01N 27/4077 73/31.01 |
| 2012/0035850 | A1* | 2/2012 | Risk ..................... G01N 1/2205 702/2 |
| 2012/0237402 | A1* | 9/2012 | Cantarelli ........... F02D 41/1448 422/111 |

OTHER PUBLICATIONS

Xinyu Wang, Selmet Inc., A New Method for Measuring Dryness During the Shell Building Process, Investment Casting Institute, 59th Technical Conference & Expo, 2012.

Julie Markee, A New Method for Measuring Dryness During the Shell Building Process, Investment Casting Institute, 59th Technical Conference & Expo, 2012.

\* cited by examiner

METHOD AND APPARATUS FOR MEASURING AND RECORDING REAL TIME ENVIRONMENTAL CONDITIONS AT TARGET SHELL LOCATIONS DURING THE SHELL BUILDING PROCESS

CROSS-REFERENCE TO RELATED APPLICATION

This application claims priority under 35 U.S.C. §119(e)(1) to U.S. Ser. No. 61/710,613, filed Oct. 5, 2012, which is hereby incorporated by reference in its entirety.

FIELD OF ART

The invention concerns investment casting shell building from ceramic slurries, particularly a method and apparatus for real time monitoring and data recordation of dryness and environmental conditions at target shell locations and at target specific shell substrates while the shell is formed through iterations of dipping in ceramic slurries, sand application, and then drying.

BACKGROUND

Investment casting is an ancient process for forming metal parts by pouring molten metals or alloys into ceramic molds, referred to in the art as shells. The shells initially are formed around wax patterns, and after shelling the wax patterns are melted out leaving an internal void that is shaped and having detail of the desired part. The molten metal or alloy is poured into the internal void of the shell, then cools, thereby solidifying into the desired shape and detail of the part. After the metal or alloy has cooled and solidified, the shell is removed revealing the desired part.

Investment casting shells start out as a wax part that is matching the shape, size and detail of the desired article. The wax part is typically dipped into an aqueous ceramic slurry, coated with sand, and then dried before reiterating until the requisite thickness of the shell is obtained. The shell drying environment varies by foundry as temperature control, relative humidity management, and air movement are employed to manage and control the drying of the shell.

Critical care is taken in drying each dip layer from face coat until seal coat, as soak back from later dip coats effect the moisture level of the inner coats which may negatively impact shell strength. Adequate drying is necessary to ensure the strength of the shell and the integrity of detail of the desired article. A 'too wet' section of the interior shell substrate may cause soak back resulting in structural failure or loss of necessary article detail of the shell. A 'too dry' section of the interior shell may cause cracking or splitting resulting in failures during the article pouring process, or defects in the finished article.

After the shell building process is complete, wax is melted out of the shell leaving an internal void within the ceramic shell exacting the shape, size, and detail of the desired article. This wax removal may be performed via a number of methods including an autoclave or flash-fire dewax process. After the wax is melted out of the shell, the shells are inspected for structural failures, often times the noted failures are repaired before the shell is moved to the foundry, that is if the structural defects are discovered Prior to pouring molten metal or alloy into the internal shell void, the shell is inspected, repaired as needed, and ultimately is placed into an oven. The purpose of this 'oven' step is to burnout any organic materials, form high temperature ceramic bonds and to heat the shell to a temperature which will allow the molten metal or alloy to completely fill-out the detail prior to solidifying. Once the shell is heat cured and maintained at the desired temperature for the requisite time, the molten metal or alloy is poured, filling the internal shell void completely.

The metal or alloy is allowed to cool within the shell taking on the shape and full detail of the original wax part. After adequate cooling, the shell is removed revealing a metal casting in exacting shape and detail as the wax part. The cast part is cut off the runner and processed to the required specifications.

During each of the described steps in the investment casting process a number of variables impact the subsequent steps that ultimately affect finished casting article quality. In an effort to assure quality control, repeatability, and effectuate an economy in production, it is critical to identify the key variables and establish operating protocols to manage the same.

Having good process control in the shell room is critical in making high quality consistent shells that produce desired casting parts. Some of key variables that need to be monitored and controlled include, but are not limited to pH, $SiO_2$ content, % polymer, slurry viscosity, shell drying, shell room temperature and relative humidity. Variations in any of these can impact the quality of the finished part.

Shell drying is likely one of the most critical variables that has proved difficult to accurately monitor and therefore control. Historically, it has been challenging to determine a reliable method or apparatus that provides real time information regarding variations in the temperature and moisture level within the shell substrates during the dipping and drying process. As discussed above, inadequate drying can cause casting defects such as excess metal, finning or even foundry run-outs. Excessive drying can result in longer processing time, in addition to surface-related casting defects such as cracks and rat-tailing. Knowing the temperature and level of dryness at the interior shell surface or within the substrates of the shell itself would provide valuable insight as to how to adjust or fine tune the dipping and drying processes to maximize efficiencies while maintaining quality control.

Prior to this invention, shell moisture or dryness monitoring had four accepted methods; visual indicator, weight loss studies, temperature and conductivity. The first two methods provide information as to the average dryness of the shell in it's entirety, with minimal to no accurate target specific data. The latter methods, temperature and conductivity can provide data at a specific location of a shell, however, both methods are limited. Measuring temperature and then inferring an estimated dryness in the internal passages of a mold can result in erroneous data if there isn't sufficient air movement to remove the moisture-saturated air. Conductivity can be an effective method to measure moisture content of the mold in a specific location, however, it is difficult to locate the probes such that substrate specific or area specific information can be measured.

While each of the described methods and apparatus tests for general shell drying, not one of the previous methods or apparatus provide accurate, reliable and repeatable testing for the specific substrates and areas most difficult to dry, including the inner passage ways, blind holes and slots. Also, later dip iterations may cause excess moisture to be absorbed into the drying shell substrates, thereby wicking back towards the wax part, creating a hidden wet area within the inner shell substrates that if not dried adequately, will cause a failure or defect.

The prior art is replete with control apparatus and methods relating to the ceramic slurry viscosity, drying methods of the shell between slurry dips, robotic dipping apparatus controlled by microprocessor, wax formulas, and exterior shell monitoring to forecast internal shell dryness. However, nothing in the prior art teaches or suggests a method or apparatus for real time monitoring and data recordation of the environmental conditions at specific target location at the shell interior, or within the shell substrates during both the slurry dipping process or shell drying periods.

REFERENCE NUMERALS

1—Wax Part
2—Shell Surface
3—Face Coat
4—Second Coat
5—Third Coat
6—Air Communication
10—Hollow Probe
20—Water Proof Breathable Membrane (WPBM)
30—Aperture
32—Vapor
40—Sensor
50—Internal Void
60—Hardwire
61—Data logger

SUMMARY OF INVENTION

This disclosure describes embodiments of apparatus and method for reliable measuring and recording in real time the environmental conditions at specific target areas within the shell interior or within the shell substrates during both the dipping and drying processes. Working embodiments of the disclosed inventive apparatus and method are directed at collection of environmental information relating to the dryness of the interior of the ceramic shell at target specific locations, including the shell areas and substrates that historically have proven the most difficult to dry.

DETAILED DESCRIPTION

Previous to this invention, the shell builder was forced to rely upon average shell dryness as estimated through visual indication, weight lost studies, temperature, and conductivity testing. The average dryness data required the shell builder to make an educational guess as to what the dryness was at the interior shell locations and the difficult to dry locations, often leading to failures, diminished detail, and critical flaws that could have been avoided had more accurate information been available.

Figure 1:
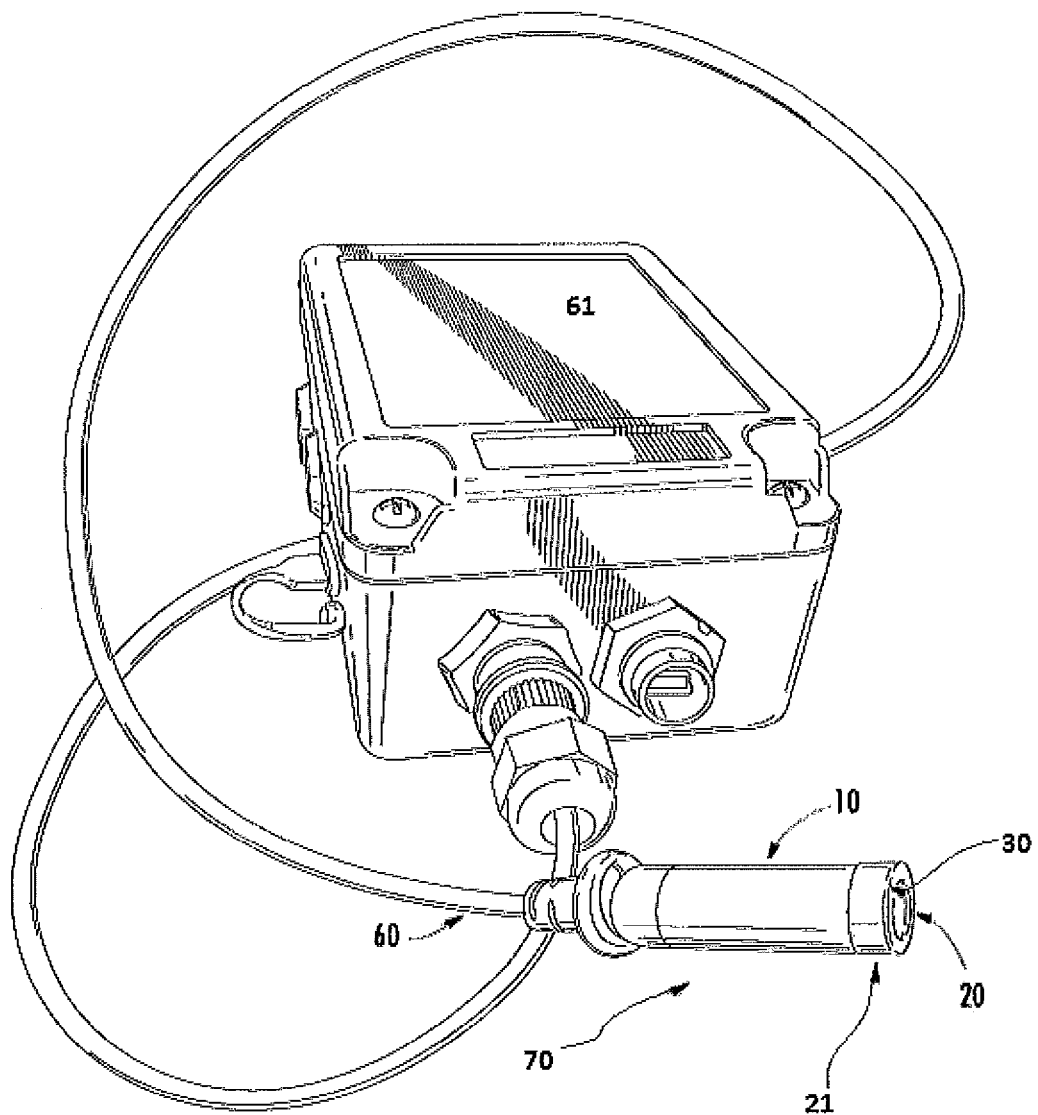
FIG. 1 is a perspective view of the inventive probe configured for use with a data logger

As shown in FIG. 1, the preferred embodiment of the inventive sensor assembly 70 is depicted as hardwired 60 to a data viewer/logger 61 which displays and records information collected by the sensor assembly 70. The preferred sensor assembly 70 includes a sensor 40 shown diagrammatically in FIGS. 2-5 as located within a hollow probe 10 having at least one aperture 30, said aperture 30 being covered by a material that allows air or vapor to permeate in communication with an internal void 50, while remaining impermeable to liquid. The aperture 30 cover material referred herein as Water Proof Breathable Membrane (WPBM) 20 stops liquid while allowing air and vapor to transfer. The WPBM 20 is secured via two-part epoxy, fittingly attached collar (as shown in FIG. 1), or other suitable securement means such as fixation by glue, band or sealant. The WPBM 20 covers the aperture 30 thereby providing a waterproof shield for the internal void 50 while still allowing vapor communication with the shell at the aperture 30 location.

Figure 2:
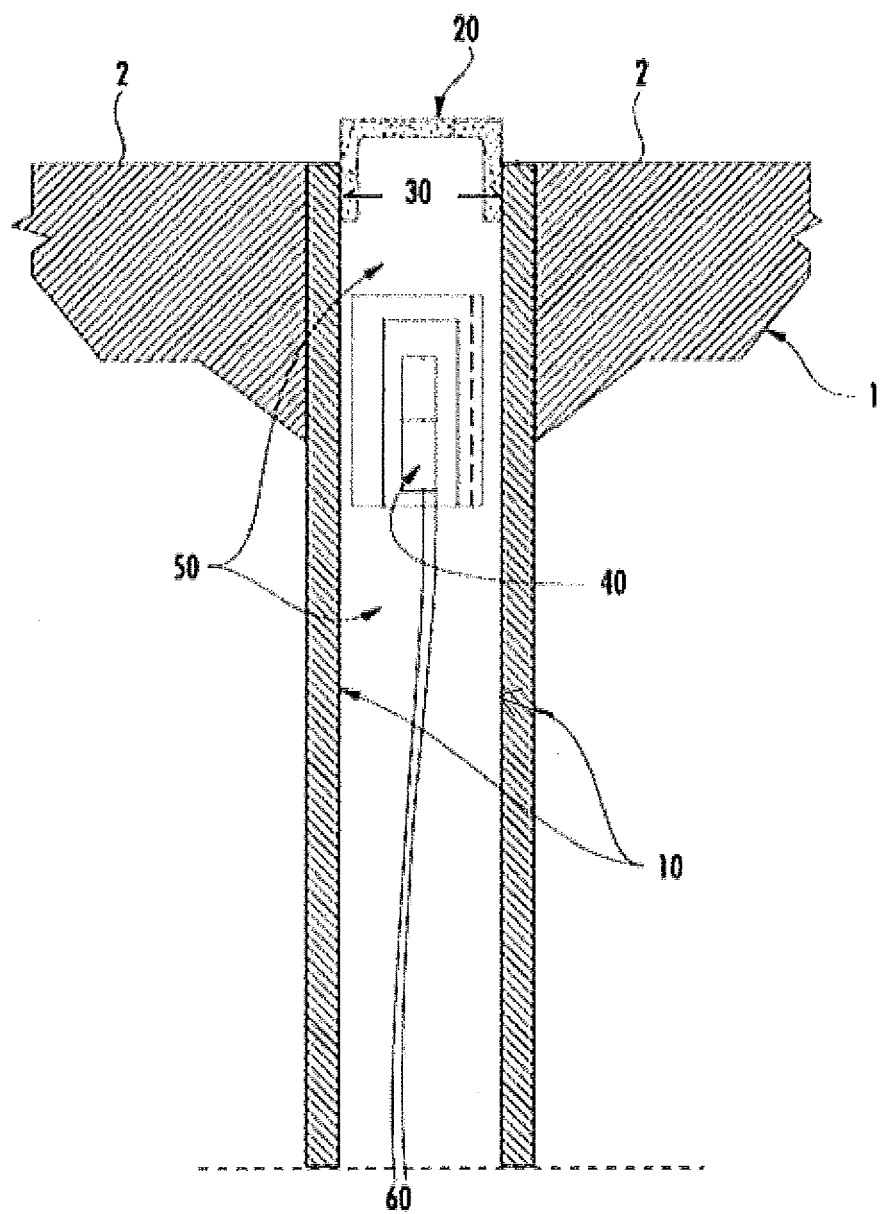
FIG. 2 is a cutaway cross section view of wax part with probe/sensor
Figure 3:
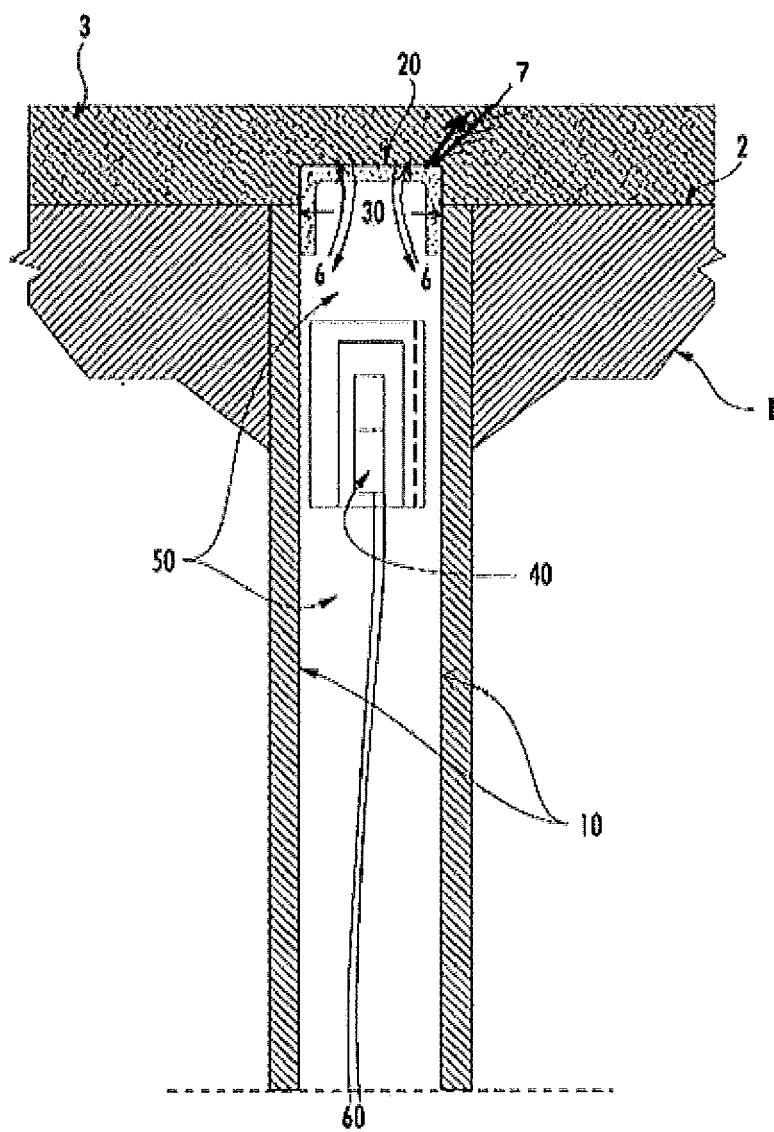
FIG. 3 is a cutaway cross section view of wax part with probe/sensor after face coat of ceramic slurry

In practice, the internal void 50 receives vapor (air with water or other matter suspended) through the aperture 30, with liquid slurry or separated water repelled by the WPBM 20. One or more sensor(s) 40 (shown in FIGS. 2-5) being located within the hollow probe 10 sense the environmental conditions within the internal void 50. The conditions within the internal void 50 prove out as accurately indicative of the conditions of the shell substrate wherein the aperture 30 is so located, thereby allowing for accurate measurement of shell substrate conditions such as, dryness, temperature and other critical substrate conditions during the shell forming process as enabled by the utilization of the inventive sensor assembly. In the preferred embodiment as depicted in FIGS. 2 and 3, when sensing the dryness at the face coat or first coat 3, the WPBM 20 covered aperture 30 is located flush with the wax part 1 exterior surface and on plane with the shell substrate of interest, here arranged as shown to sense the first coat 3. The sensor 40 senses the environment within the internal void 50, which in turn provides the sought after information as to the condition or status of the first coat 3, to include the dryness, temperature, timing of moisture gradient, and overall status of the first coat 3 during the shell building process. As one of ordinary skill will immediately realize, by locating the covered aperture 30 as projecting away from the wax part 1 exterior surface provides opportunity to collect data within the shell at the desired shell substrates levels during the forming process. The preferred embodiment arrangement with the aperture 30 being located proximal to the wax part 1 is just one embodiment relative to gaining information at a particular location and substrate.

The connection of the sensor assembly 70 to the data review/logger 61 may also be facilitated by RF signal, wireless device or hardwired 60 to a data-logger that gathers sensor 40 output in real time, displays and records the same to a storage media or other real time control device.

The sensor 40 may be of many commercial off the shelf types, measuring environmental conditions ranging from humidity, temperature, moisture, dryness, conductivity, infrared signatures, relative pressure, pH, or residual gasses. After the shell is finished and sensing or testing completed, the relatively expensive sensor 40 element and waterproof breathable membrane 20 may be removed for re-use, while the spent wax part 1 and inexpensive hollow probe 10 are melted out.

The waterproof breathable membrane 20 may be of various commercially available materials to include multi-ply mesh materials or Teflon® enhanced fabrics having substrates sandwiched between an outer fabric shell and a tricot mesh. The material may also have different coatings such as polyurethane or water repellent finish that meet the waterproof breathable membrane requirements. Gortex® brand super breathable material also is suitable for this application. Mesh fabrics or fine screens that allow air movement while also impervious to water are preferred, but any waterproof breathable membrane 20 will suffice.

The data logger may be digital or analog, and the storage media can be of any type that that is compatible with the data logger. Laptop, smart phone, or other available microprocessors may be implemented depending on application and connection method with the sensor 40.

As diagrammatically shown in FIG. 2, the shell surface 2 is approximately OD plane with the aperture 30, the aperture 30 being located and positioned such that the WPBM 20 covers the aperture 30 and will be in contact with the ceramic slurry at the area and depth of interest per hollow probe 10 location. The aqueous slurry of the face coat 3 does not penetrate the internal void 50, as the WPBM 20 maintains a substantially waterproof seal while allowing vapor communication 6 between the sensor 40 and the face coat 3 through the aperture 30. As each subsequent coat is applied, the communicating vapor 6 is sensed, as the vapor 6 proves equivalent to the relative dryness, temperature, and other characteristics of the shell at the aperture 30 location. The internal void 50 is monitored by the sensor 40, thereby providing information as to the dryness of shell substrate of interest. Other information is also easily sensed within the internal void 50 to include but not be limited by the relative temperature deltas during the drying or dipping period, timing of the process steps, relative amounts of soak back from the subsequent slurry dips, and the time it took for the moisture gradient to move. By maintaining real time sensor 40 monitoring within the internal void 50, the shell building process can be adjusted to accommodate the actual conditions of the shell substrate of interest.

In one of the more robust embodiments, the hollow probe 10 is integrally formed within the wax part 1 so as not to require the hollow tube material. The wax part 1 having an internal void 50 that is large enough to receive a sensor 40, the internal void 50 having an aperture 30 that is covered with a WPBM 20 as discussed above. Integrally forming the internal void 50 within the wax part 1 reduces component counts, and simplifies set up.

Figure 4:
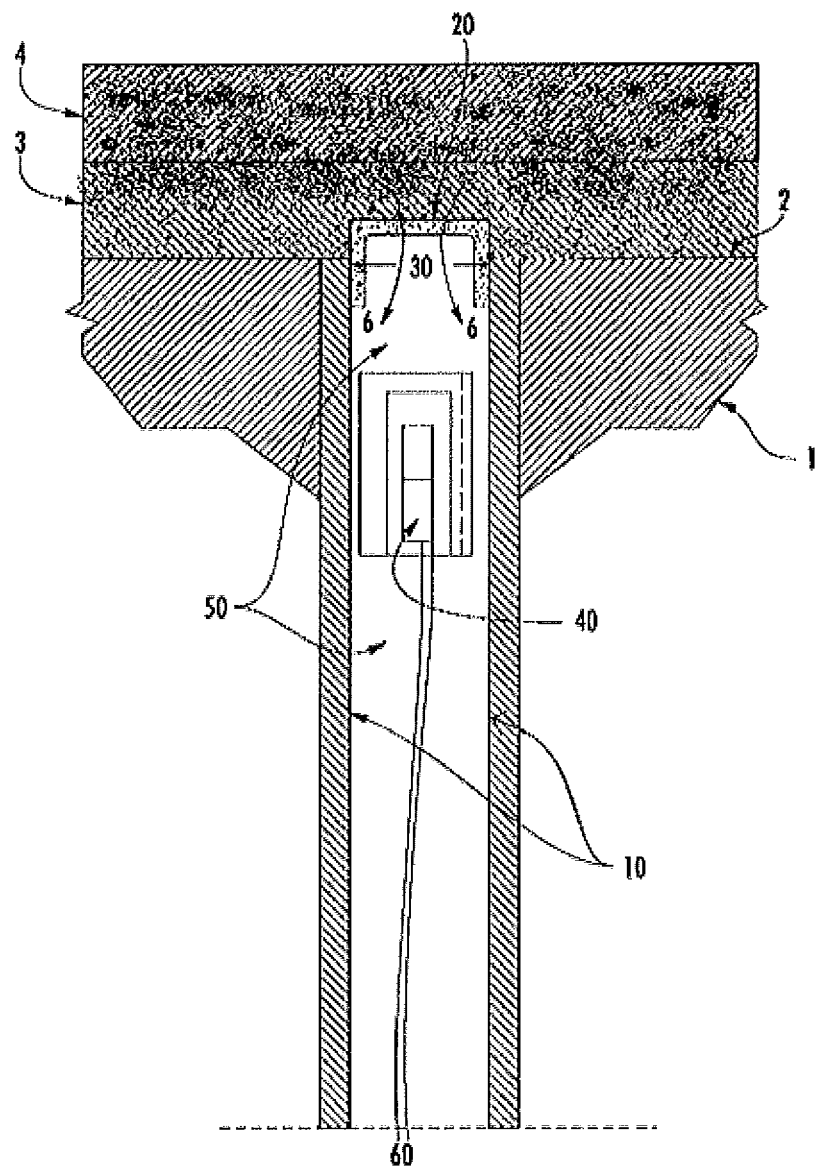
FIG. 4 is a cutaway cross section of wax part with probe/sensor after second coat of ceramic slurry

As depicted, a next slurry dip provides a second coat 4 of ceramic slurry as depicted in FIG. 4 where the second coat 4 is relatively wet illustrated as darker than the face coat 3 that is relatively dry after having some drying time. The different shades diagrammatically represent different dryness or wetness conditions of the shell substrates during the shell building process that are readily sensed by the sensor 40 or combination of sensors 40. The relative dryness or wetness moves within the shell substrates, as being soaked or wicked back and forth as gradients of relative moisture. Understanding and predicting the flow of moisture and dissipation of the same within the shell substrates during the shell building process proves paramount to quality assurance.

Figure 5:
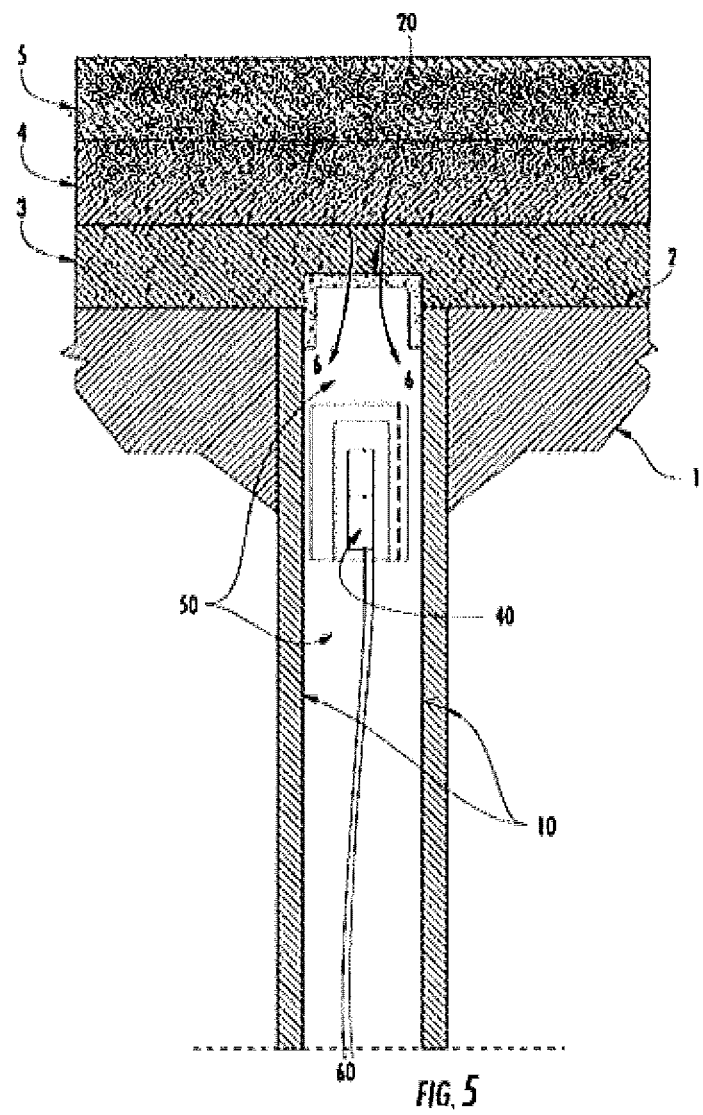
FIG. 5 is a cutaway cross section of wax part with probe/sensor after third coat of ceramic slurry

As discussed herein and shown in FIGS. 3-5, vapor 32 communicates through the probe 10 aperture 30, passing through the WPBM 20 into the internal void 50, to be sensed by the sensor 40. Depending on the sensor or combinations of sensor(s) 40, the relative humidity, temperature, or other physical attributes are measured within the internal void 50 as introduced by the vapor 6 communicating from the shell substrate, through the aperture 30. The vapor 6 from the shell substrate has substantially the same moisture content and temperature as does the shell substrate itself, meaning the less humidity in the vapor 6, the more dry the shell substrate and vice versa. Temperature is also accurately determined at the aperture 30 location by measuring the temperature within the internal void 50, which imparts information involving both the drying time and other chemical and non-chemical reactions.

Reiterative slurry dips provide additional coats, as diagrammatically shown in FIG. 4, wherein the third coat 5 is relatively wet illustrated darker. The earlier discussed wicking or soaking back towards the wax part 1 is illustrated in various shades of grey and black in the face coat 3 and second coat 4. It is well known in the art that the soak back rehydrates the inner coats of the ceramic shell as later coats are applied. The historic problem of not knowing how much soak back has occurred or to what level of dryness the inner substrates have achieved is solved by the disclosed invention.

At the conclusion of the shell building process, after the desired target location environmental data is collected but before the dewaxing process, the sensor 40 and sometimes the WPBM 20 and the hollow probe 10 may be removed from the wax part 1 or shell for reuse. In one embodiment wherein the probe 10 is constructed of compatible wax, the probe 10 is left within the wax part 1 during the dewaxing process.

As the shell building process continues as depicted in FIGS. 3-5, which often involves more than three dipping iterations, a too wet inner coat may never adequately dry causing critical flaws or failures during the dewax process or metal pouring in the foundry. Alternatively, a too dry inner coat could result in a split or crack caused by the lack of hydration, also making the shell susceptible to failures and flaws that can't be seen or determined from the outside of the shell. Benefiting from real time environmental information for hard to dry target locations allows the shell builder to accurately determine the necessary drying time between slurry dips based on target specific information, rather than guessing based on the average dryness of the entire shell. Also and perhaps most importantly, the shell builder will know that she has a soak back issue or other potential for a critical flaw before proceeding with further reiterative coats that would only serve to bury or hide the internal shell defect.

This invention should not be limited to the particular embodiments disclosed herein, but includes all embodiments within the spirit and scope of the disclosed invention as claimed.

What is claimed is:

1. A method to determine the condition of an investment casting shell substrate during the shell building process, comprising the steps of: providing a hollow probe 10, the hollow probe 10 having an aperture 30; covering the aperture 30 with a WPBM 20 thereby creating a liquid free internal void 50 within the hollow probe 10; locating the aperture 30 adjacent to a shell substrate of interest; and enclosing a humidity sensor 40 within the internal void 50 for sensing the vapor communicating through the aperture 30 from the shell substrate adjacent to the aperture 30 location.

2. The method to determine the condition of an investment casting shell substrate during the shell building process according to claim 1, wherein the hollow probe 10 has more than one aperture 30.

3. The method to determine the condition of an investment casting shell substrate during the shell building process according to claim 1, wherein the sensor 40 senses relative humidity, temperature, or both.

4. The method to determine the condition of an investment casting shell substrate during the shell building process according to claim 1, wherein the hollow probe 10 is integrally formed within a wax part 1.

5. An investment casting shell substrate sensor assembly for measuring the conditions of the shell substrate during the shell building process, comprising:
- a hollow probe 10 having one aperture 30 and being integrally constructed within a wax part 1;
- a water proof breathable membrane (WPBM) 20 that is constructed and arranged to cover the aperture 30 thereby creating a liquid free internal void 50 within the hollow probe 10; and
- a sensor 40 enclosed within the internal void 50 senses the vapor communicating through the aperture 30 from a shell substrate adjacent to the aperture 30 location, the sensor 40 thereby providing information as to the conditions at the shell substrate.

\* \* \* \* \*